United States Patent [19]

Stetter

[11] Patent Number: 4,847,594

[45] Date of Patent: Jul. 11, 1989

[54] SENSOR FOR DETECTING THE EXHAUSTION OF AN ADSORBENT BED

[75] Inventor: Joseph R. Stetter, Naperville, Ill.

[73] Assignee: Transducer Research, Inc., Naperville, Ill.

[21] Appl. No.: 174,180

[22] Filed: Mar. 28, 1988

[51] Int. Cl.$^4$ ............................................. G08B 21/00
[52] U.S. Cl. ................................ 340/540; 73/27 R; 324/61 P; 324/65 P; 340/632
[58] Field of Search ............... 340/540, 632, 633, 634; 73/27 R, 23; 422/88; 55/74, 75; 324/61 P, 65 P

[56] References Cited

U.S. PATENT DOCUMENTS

| | | | |
|---|---|---|---|
| 2,951,156 | 8/1960 | Miller | 250/306 |
| 3,902,485 | 9/1975 | Wallace | 128/205.27 |
| 4,095,965 | 6/1978 | Neumann et al. | 55/270 |
| 4,224,595 | 9/1980 | Dolan | 338/34 |
| 4,453,151 | 6/1984 | Leary et al. | 73/23 |
| 4,509,034 | 4/1985 | Sakai | 73/27 R |
| 4,646,066 | 2/1987 | Baughman et al. | 340/540 |

OTHER PUBLICATIONS

Wohltjen, Jank., "Chemical Microsensors and Microinstrumentation", *Analytical Chemistry*, vol. 56, No. 1, Jan. 1984, pp. 87–103.

Lukaszewicz et al., "Semiconducting Carbons for Water and Ethanol", Proc. of the 2nd Int. Meet. on Chemical Sensors, Bordeaux, 1986, pp. 146–149.

Jones et al., "High Temperature Intermittent Operation of NO$_2$ Sensors Based on Phthalocyanine Thick Films," Proc. of the 2nd Int. Meet. on Chemical Sensors, Bordeaux, 1986, pp. 167–170.

*Primary Examiner*—Glen R. Swann, III
*Attorney, Agent, or Firm*—Larson and Taylor

[57] ABSTRACT

A sensor includes a vapor sensitive medium and a means for monitoring at least one property of the vapor sensitive medium. The vapor sensitive medium is chosen such that it exhibits a response to the vapors absorbed by an absorbent bed which is substantially the same as the response of the absorbent to the vapors absorbed. The monitored property is a function of the response of the vapor sensitive medium to the vapors absorbed. Also disclosed are an absorbent bed alarm system employing the sensor and a filter cartridge which employs the adsorbent bed alarm system.

20 Claims, 6 Drawing Sheets

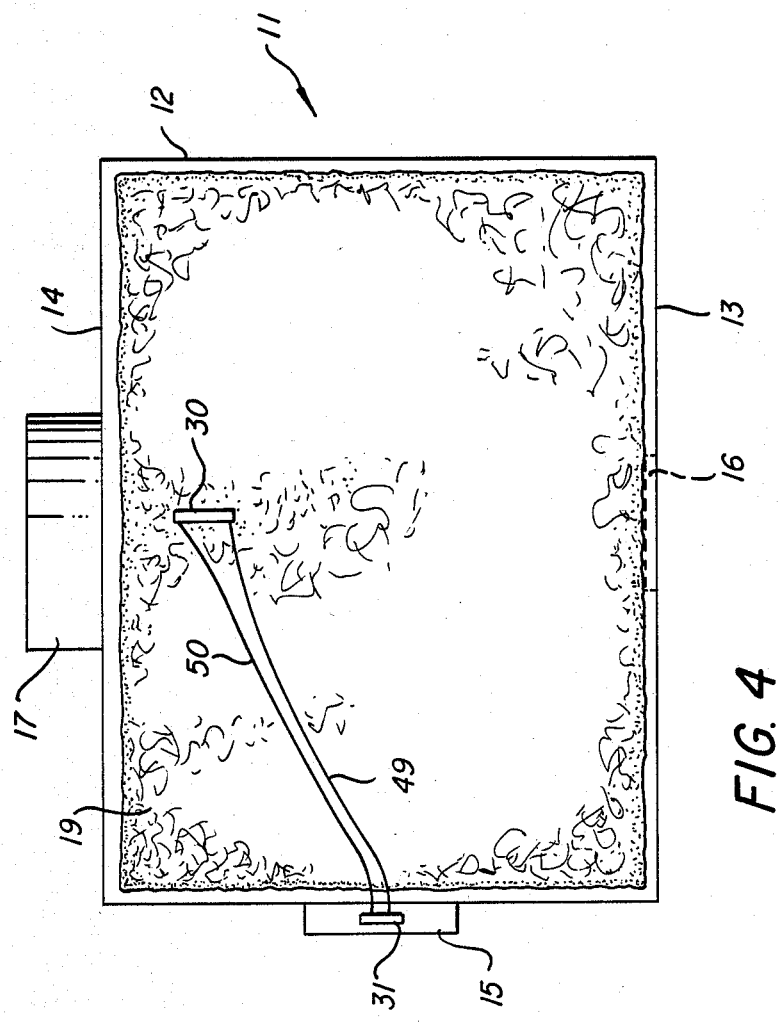

SENSOR FOR DETECTING THE EXHAUSTION OF AN ADSORBENT BED

FIELD OF THE INVENTION

The present invention relates to a sensor for use in detecting the exhaustion of an adsorbent bed and to adsorbent beds employing such sensors.

BACKGROUND OF THE INVENTION

Filters and respirators worn over the face are used as protection against toxic vapors in many occupations. At present there is no fast and accurate way to determine the status of a used or partially used respirator device. Proposed approaches to estimating the useful life have included accurate logging of use time, periodic breakthrough testing, and color change indicators. These methods merely estimate the status of the respirator device and, as is the case with the breakthrough testing, often result in the exhaustion of the filter thereby making the respirator useless. The ideal solution to this problem consists of a filter cannister which incorporates an indicator or alarm which signals the end of the respirator's useful lifetime.

Ideally, a sensor for detecting the exhaustion of an adsorbent bed in a respirator should detect all vapors the adsorbent is designed to remove. Further, the sensor is required to operate over the entire range of temperatures and pressures which are normally encountered in adsorbent use. This means that the sensor must be capable of operating in temperatures from $-65°$ to $110°$ F. and pressures from 0.8 to 1.2 atmospheres for personal protection applications and can be designed for severe pressure, vacuum, humidity and temperature conditions present in industrial and military use. The sensor must also be capable of enduring all conditions of use for an adsorbent such as being attitude insensitive, shock and vibration resistant, storage stable for as long as the adsorbent is stored and the sensor must also last as long in use as the adsorbent. Finally, the sensor must have a response time which gives the user sufficient warning of adsorbent bed exhaustion.

One approach to this problem is to detect the presence of all possible toxic gases that could emanate from the adsorbent by using a sensing device which is sensitive to all the toxic gases which the adsorbent bed is designed to adsorb. An example of this method can be seen in U.S. Pat. No. 3,902,485 (Wallace) issued on Sept. 2, 1975. In this method, spaced electrodes, at least one of which is coated with a basic nitrogen-containing polymer of high electrical resistance, project into an electrical conducting medium such as activated charcoal in a container. The coated electrode is connected in series with signalling means which puts out an audio and/or visual signal. The coating on the electrode forms an electrically conducting quaternary ammonium salt in the presence of selected and predetermined toxic gases to thereby lower the electrical resistance of the polymer coating and complete the electrical circuit between electrodes through the charcoal. This activates the signalling means to generate an alarm signal.

Sensors designed for detecting the presence of toxic gases for use in combination with conventional gas filter breathing apparatus suffer from several drawbacks. First, these sensors are generally relatively expensive when compared with the cost of the adsorbent bed. Second, the typical sensors are only sensitive to a few or several of the potentially toxic gases, i.e., the sensors are somewhat selective in their response to gases and vapors. Further, sensors detecting gases in the adsorbent bed output must detect everything and anything that comes through the bed. This is a difficult problem since it is nearly impossible to predict what toxic gases the respirator adsorbent and the user of a respirator may be exposed to. This makes design of sensors capable of detecting everything that comes through the bed very difficult and virtually impossible. In addition, sensors detecting the presence of toxic gases in the adsorbent bed will have significantly different reactivity than the adsorbent bed itself for the same gas or vapor. This will often cause premature signalling of adsorbent bed exhaustion or, even more dangerous, the alarm signal will be generated too late and toxic gases will pass through the adsorbent bed to the user.

Accordingly, there is a need in the art for an improved sensor device which can be used in combination with an adsorbent bed material to provide a real-time warning of the exhaustion of the adsorbent bed and thereby prevent human exposure to harmful vapors. In addition to having the appropriate analytical response described above, the sensor must also be low-cost, low-power, tiny, stable, rugged and completely reliable.

SUMMARY OF THE INVENTION

The present invention relates to a sensor useful in detecting the exhaustion of an adsorbent bed. The sensor includes a vapor sensitive medium having a response to the vapors adsorbed by the adsorbent bed which is substantially the same as the response of the adsorbent to the vapors adsorbed. The sensor also includes a means for monitoring a property of the vapor sensitive medium which is related to the response of the vapor sensitive medium to the vapors adsorbed by the adsorbent.

In a second embodiment, the present invention relates to an adsorbent bed safety alarm system for detecting and signalling the exhaustion of an adsorbent bed. The alarm system includes a sensor means and a means for generating an alarm signal. The sensor means includes a vapor sensitive medium having a response to the vapors adsorbed by the adsorbent bed which is substantially the same as the response of the adsorbent to the vapors being adsorbed. The sensor means also includes a means for monitoring a property of the vapor sensitive medium that is related to the response of the vapor sensitive medium to the vapors adsorbed by the adsorbent. The means for generating an alarm signal is responsive to a change in the property monitored by the means for monitoring.

In a third embodiment, the present invention relates to an apparatus for use in adsorbing harmful or undesirable vapors that signals the exhaustion of the adsorbent material to prevent flow of harmful or undesirable vapors through the apparatus. The apparatus includes a housing having an inlet means and outlet means. It also has an adsorbent bed housed within the housing. Located in the adsorbent bed is a sensor means. The sensor means includes a vapor sensitive medium having a response to the vapors adsorbed by the adsorbent bed which is substantially the same as the response of the adsorbent to the vapors being adsorbed. The sensor means also includes a means for monitoring a property of the vapor sensitive medium which is related to this response of the vapor sensitive medium to the vapors adsorbed by the adsorbent. Finally, the apparatus includes a means for generating an alarm signal. This means for generating an alarm signal is responsive to a change in the property of the vapor sensitive material monitored by the monitoring means.

It is the primary object of the present invention to provide a low-power, low-cost, reliable sensor that can be incorporated into respirator devices to provide a real-time warning of the exhaustion of the adsorbent bed.

It is a further object of the present invention to provide a sensor for use in adsorbent beds having substantially the same response to the vapors being adsorbed as the response of the adsorbent material to the vapors being adsorbed. This means the sensor responds to substantially all of the vapors that the adsorbent is designed to remove.

It is a still further object of the present invention to provide a sensor for use in an adsorbent bed alarm system which minimizes the number of false alarms and non-occurence of alarms which should have occurred.

It is a still further object of the present invention to provide a sensor for use in an adsorbent bed alarm system which responds to only the materials which the adsorbent bed is designed to adsorb.

These and other objects of the present invention will be apparent to one of ordinary skill in the art from the detailed description of the invention which follows. While the descriptions refer to a personal protective device and a carbonaceous adsorbent, the principle can be easily applied to fixed-bed adsorbent for purifying and deodorizing air and other adsorbents such as molecular sieves, polymeric materials, and chromatographic stationary phases.

BRIEF DESCRIPTION OF THE DRAWINGS

FIG. 4 is a cross-sectional view of a filter cartridge outfitted with an alarm system in accordance with the present invention.

DETAILED DESCRIPTION OF THE PREFERRED EMBODIMENTS

Figure 1:
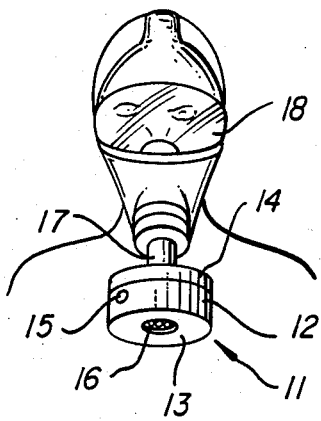
FIG. 1 is a front view in perspective of a man wearing a chemical filter breathing apparatus with alarm system in accordance with the present invention.

The chemical filter breathing apparatus portion of FIG. 1 is of conventional chin type such as type GMP produced by Mine Safety Appliances Company of Pittsburgh, Pennsylvania. Because of its limited capacity, this device is recommended by Mine Safety Appliances Company for respiratory protection against toxic gases and vapors in concentrations not in excess of 0.5% by volume. This breathing apparatus is illustrated in conjunction with an alarm system in accordance with the present invention. It includes a filter cartridge 11 consisting of an oval-shaped body 12, bottom closure wall 13 and top closure wall 14 which are provided for closing the open lower and upper ends of body 12. Bottom closure wall 13 is provided with a screen opening 16 which serves as the inlet to filter cartridge 11 and is sealable when filter cartridge 11 is not in use. In a conventional breathing apparatus, a filter (not shown) is mounted in the bottom of filter cartridge 11 for filtering particulate material such as toxic dust and the like. A pipe 17 provides gas communication between an opening in top wall 14 and face mask 18 and serves as the outlet of filter cartridge 11. Body 12 defines an open gas passageway through filter cartridge 11 so that the respiratory tract of the wearer is in communication with air from the environment after filtering through filter cartridge 11. Body 12 also includes an alarm housing 15 located thereon which houses the circuitry for the alarm system.

Figure 2:
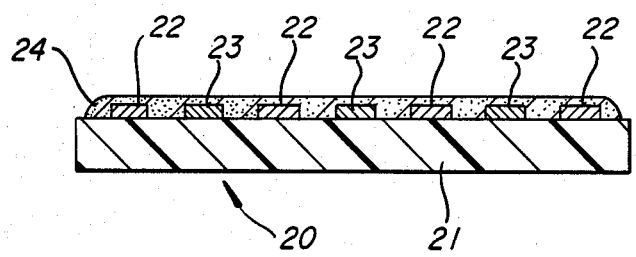
FIG. 2 is a cross sectional view of sensor in accordance with the present invention having interdigitated electrodes and an adsorbent coating thereon.

Referring now to FIG. 2 there is shown a vapor sensor 20 which includes a substrate 21, a first electrode 22 and a second electrode 23. Coated over electrodes 22 and 23 is a vapor sensitive medium 24. The first electrode 22 and second electrode 23 are interdigitated in this embodiment. Interdigitization of the electrodes is the preferred electrode configuration.

Figure 3:
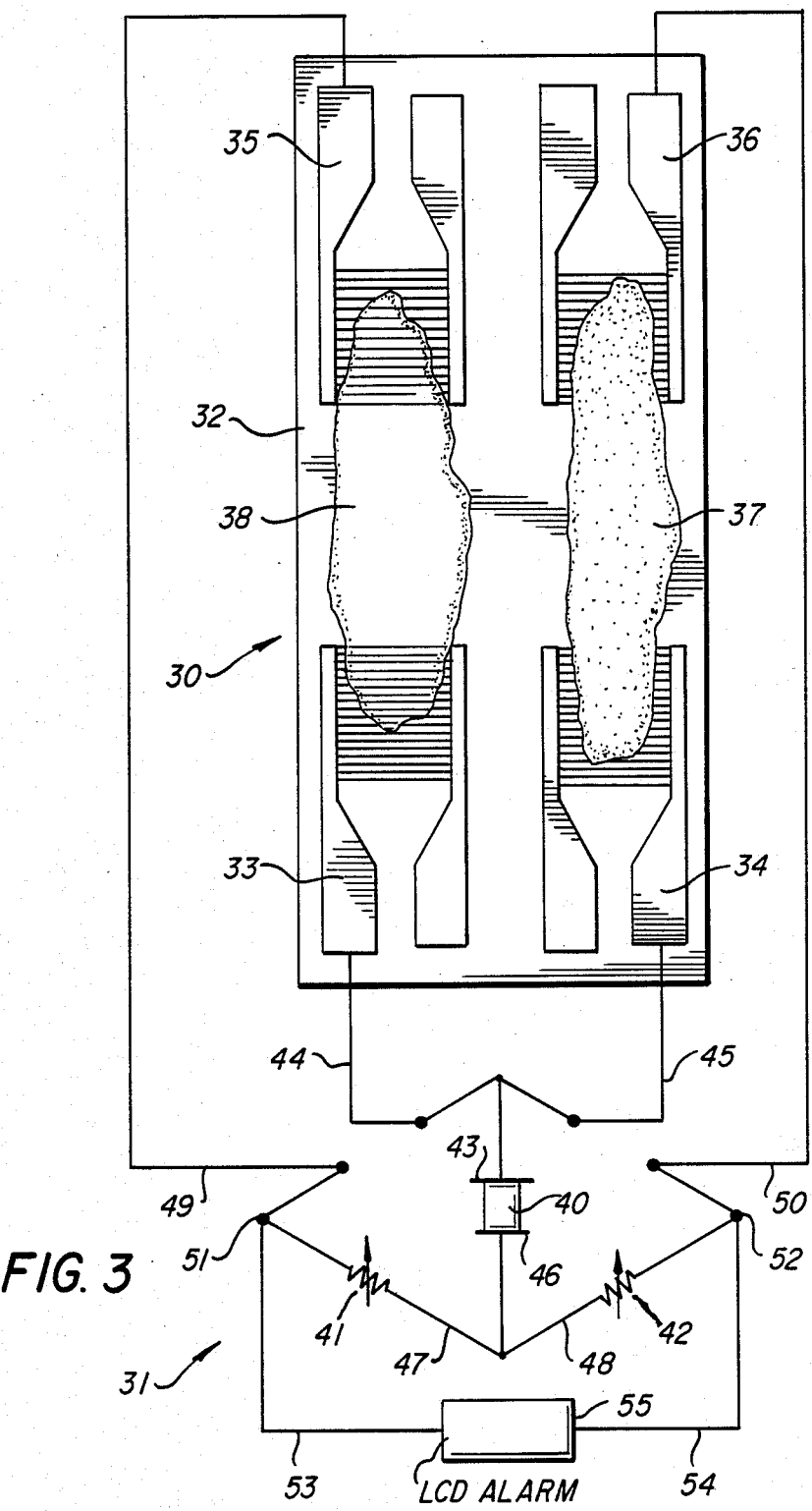
FIG. 3 is a plan view of an alternate embodiment of a sensor in accordance with the present invention, including circuitry.

Referring now to FIG. 3 there is shown an alarm system in accordance with the present invention. The alarm system includes a sensor portion 30 and circuitry 31. Sensor portion 30 is made up of a substrate 32 having on its surface a first electrode 33, a first reference electrode 35, a second electrode 34 an a second reference electrode 36. Also on the surface of substrate 32 is a passive coating 37 and an active coating 38 which are both made up of vapor sensitive material. The passive coating 37 is in contact with, and adheres to the second electrode 34 and the second reference electrode 36. The active coating 38 is in contact with, and adheres to the first electrode 33 and the first reference electrode 35. In this embodiment, the electrodes 33, 34 and the reference electrodes 35, 36 are identical and can be interchanged appropriately.

The circuitry 31 includes a lithium battery 40, a first current limiting resistor 41 and a second current limiting resistor 42. The first terminal 43 of the lithium battery 40 is connected by lines 44 and 45 to first electrode 33 and second electrode 34 respectively. The second terminal 46 of the lithium battery 40 is connected to first resistor 41 and second resistor 42 by lines 47 and 48 respectively. Wire 49 connects first resistor 41 to first reference electrode 35 and wire 50 connects second resistor 42 to second reference electrode 36. Wire 49 is also connected at junction 51 to connection 53 which leads to LCD alarm 55. Wire 50 is also connected at junction 52 by connection 54 which leads to LCD alarm 55. Connections may also be made to the other half of each of the electrodes 33, 34, 35, 36 since they are also resistive vapor-sensitive elements and they can be used in more elaborate circuitry as redundant measurements that add reliability, stability and dynamic range to the device. The LCD alarm contains all of the required components to signal an imbalance or change in the sensor/bridge circuit. Of course, this is only one example of the many ways that can be chosen to measure and display the changes that occur in the vapor-sensitive element. Any circuit that can make the appropriate electrical measurement and satisfy the requirement for size and performance for the device to be operable in the field can be used with the sensor element.

Referring to FIG. 4 there is shown filter cartridge 11 having a body 12, a bottom closure wall 13, a top closure wall 14, alarm housing 15, screen opening 16, and pipe 17. Inside the body 12 is a filter 19 made up of an adsorbent material such as charcoal. Shown inside the alarm housing 15 is circuitry 31 which is connected to sensor portion 30 by lines 49 and 50. Sensor portion 30 is located at a point closer to the pipe 17 (outlet) of the filter cartridge 11 than to the screen opening 16 (inlet) in this figure.

In the simplest embodiment of the present invention the vapor sensor 20 shown in FIG. 2 includes a substrate 21 which may be fabricated from an inert material. On the surface of the substrate 21 are a first electrode 22 and a second electrode 23 which are preferably interdigitated. These electrodes may be fabricated from any suitable conductive material of which gold, platinum, silver, or carbon are examples of preferred materials. Electrodes 22, 23 are formed on the surface of substrate 21 by any conventional method such as vapor deposition. It is desirable to place electrodes 22, 23 close together and to provide long electrode edges in order to minimize effects due to the non-uniformity of the coating of vapor sensitive medium 24 on electrodes 22, 23.

Vapor sensitive medium 24 preferably covers the entire surface of both first electrode 22 and second electrode 23. Vapor sensitive medium 24 is selected such that it has a response to the vapors being adsorbed by the filter 19 which is substantially the same as the response of the adsorbent in the filter 19 to the vapors being adsorbed. The most preferred embodiment of the present invention employs a vapor sensitive medium 24 which is the same material as that used as the adsorbent in the filter 19. In this manner, it is assured that the response of the vapor sensitive medium 24 to the vapors is the same as the response of the adsorbent to vapors. It is not necessary that the vapor sensitive medium 24 be of typical electrolytic materials. Rather, the important factor is that the vapor sensitive medium 24 exhibits a change in resistance or other measurable property upon contact with the vapors which the adsorbent is designed to adsorb. Thus, some examples of adsorbents which are useful as the vapor sensitive medium 24 in the present invention are silica, silica gel, alumina, a molecular sieve, drying agents and the like. The vapor sensitive medium 24 is generally from about $5.0 \times 10^{-8}$ cm to about 0.1 cm in thickness and preferably from $5.0 \times 10^{-6}$ cm to $1.0 \times 10^{-2}$ cm thick. However, the vapor sensitive medium 24 may be thicker or thinner depending upon the sensitivity and response time desired of the sensor.

It is particularly important in the present invention to obtain a response to the vapors being adsorbed which is substantially the same as the response of the adsorbent in the filter 19 to the vapors being adsorbed. By substantially the same response it is meant that the vapor sensitive medium 24 will exhibit a change in a measurable property, such as resistance, impedance, capacitance, weight, temperature, photo-properties, heat flow, piezoelectricity, pyroelectricity or a measurable property that can be easily sensed by the sensor (vapor-sensitive device) when it is exposed to the same conditions under which adsorption of vapors by the adsorbent will occur. The change in the measurable property must be, in some way, proportional to the amount of adsorption by the adsorbent under those conditions. In the simplest case the same material is used as both adsorbent and vapor sensitive medium 24. Upon exposure to vapors under equivalent conditions both the adsorbent and vapor sensitive medium 24 will adsorb the vapors at the same rate and thus both exhibit the same response, namely a response to the vapors that is proportional to the extent of adsorption. Then it is a simple matter to measure a property of the vapor sensitive medium 24 which changes upon vapor adsorption and thence to calibrate the changes in the measured property with various vapor concentrations to obtain a reliable indicator of how much adsorption is occurring at the location of the vapor sensitive medium 24 in the adsorbent bed. This, in combination with other factors discussed below, can be used to determine the threshold level (amount of change in the measurable property) at which the alarm will be triggered by the sensor.

The present invention takes a different approach than the prior art to determine the point of exhaustion of the adsorbent material in an adsorbent bed. In fact, because the present invention contemplates using the adsorbent material as the vapor sensing material, the present invention detects the state of the adsorbent surface instead of the individual gases or gas mixtures coming through the bed, as is done in the prior art. For example, a vapor sensitive medium 24 of charcoal can be employed inside a charcoal adsorbent bed. As long as the charcoal adsorbent surface is active, vapor sensitive medium 24 in the bed remains substantially unaffected by the vapors because they do not reach the embedded sensor since the vapors are adsorbed by the fresh adsorbent. As exhaustion of the charcoal adsorbent bed approaches, vapor contaminants will reach the surface of the vapor sensitive medium 24 and vapor sensitive medium 24 will become contaminated. This contamination by the vapor proceeds in the same manner as vapor adsorption by the charcoal adsorbent bed. This design requires that those vapors that adsorb and contaminate the adsorbent will adsorb and contaminate the vapor sensitive medium 24, and, most importantly, gases that do not adsorb ($CH_4$ on charcoal) in the adsorbent do not contaminate the vapor sensitive medium 24. Thus, the sensor detects the "state of the adsorbent." The adsorption of vapor by vapor sensitive medium 24 causes a change in the properties of vapor sensitive medium 24 on the vapor sensor 20 which is analagous to the change in properties in the adsorbent resulting from vapor adsorption. This change in properties is detected by the circuitry 31. The circuitry 31 is preferably fabricated to detect a change in a single, easily detected property of vapor sensitive medium 24 which property is altered as a function of vapor adsorption by vapor sensitive medium 24. Once the change in the detected property exceeds a preset threshold level it sets off an alarm which indicates the approaching exhaustion of the adsorbent bed.

Two extremely important advantages are obtained by employing a vapor sensitive medium 24 which exhibits substantially the same response to the vapors as the adsorbent used in the adsorbent bed. First, the vapor sensitive medium 24 will have a low cost relative to the adsorbent bed (often its cost is the same as the adsorbent). Thus, the addition of an alarm system in accordance with the present invention will not make respiratory filter cartridges prohibitively expensive or large. In comparison, the use of standard gas sensors known in the art as the vapor sensor will generally add more than $200 to the cost of a respiratory filter cartridge thus making the cartridge prohibitively expensive. Size is also important and the device of the present invention can be very small and on the order of micron-sized, if required.

The second advantage is extremely important. The use of a vapor sensitive medium 24 which is the same material as the adsorbent of the adsorbent bed or which exhibits substantially the same response to the vapors as the adsorbent bed will ensure the same response to each and every vapor present in the filter cartridge for the vapor sensitive medium 24 as for the adsorbent bed. Accordingly, the vapor sensor 20 will only respond to the vapors that the adsorbent bed adsorbs. Thus, the vapor sensor 20 does not give false alarms as a result of exposure to vapors not interactive with the adsorbent. In addition, the vapor sensor 20 will respond to all vapors which are active with the adsorbent. This makes the vapor sensor 20 of the present invention highly reliable for detecting the exhaustion of an adsorbent bed. Reliability is an important feature of a sensor of this type since a sensor failure may cause human exposure to toxic vapors.

The coating of vapor sensitive medium 24 may be prepared by dissolving a silicon rubber adhesive in methylene chloride and suspending the vapor sensitive material in this solution. The suspension is then applied to the surface of the substrate 21, first electrode 22 and second electrode 23 using a proprietary spin-coating technique for the preparation of micro-sensors which is disclosed in our co-pending U.S. Patent Application Ser. No. 07/53,722 filed on May 26, 1987, now U.S. Pat. No. 4,795,543, which is hereby incorporated by reference. The most preferred microsensors for use in the present invention are those described in my copending U.S. Patent Application Ser. No. 07/053,705 filed on May 26, 1987 now abandoned and replaced by Application Ser. No. 230,684 filed Aug. 10, 1988, which is hereby incorporated by reference. Thick film coatings and carbonaceous coatings are also feasible by processes such as silk screening, sputtering, painting and chemical or physical deposition processes.

Referring now to the alternate embodiment shown in FIG. 3, which is the preferred embodiment of the present invention, it has been determined that the ideal sensor is a relatively high impedance device having four electrodes. This consists of two pairs of two electrodes. One pair of electrodes is an active sensor area and the other is passive and provides temperature compensation for the sensor device if required by the application. More particularly, all four electrodes 33, 34, 35, 36 may be substantially identical. Electrodes 33 and 35 are covered with an active coating 38 of vapor sensitive medium 24. The active coating is preferably a material having a response to the vapors being adsorbed which is substantially similar to the response of the adsorbent bed to the vapors being adsorbed. Electrodes 34 and 36 are coated with a passive coating 37 which responds identically to active coating 38 except that it does not respond to the vapor being adsorbed by the adsorbent bed. However, passive coating 37 responds to temperature variations in a manner which is substantially identical to the response of active coating 38 to temperature variations. In this manner, a convenient method of signal correction for temperature effects is obtained. As a result, a sensor of this type is capable of operating over a large temperature range. Because it is similar in performance to the adsorbent, it can be used over any Temperature or Pressure (or other conditions such as relative humidity, etc.) range as the adsorbent itself. The particular geometry shown in FIG. 3 also enhances the thermal stability of the sensor.

Referring now to circuitry 31 shown in FIG. 3 it includes first current limiting resistor 41 and second current limiting resistor 42 having resistances of R1 and R2 respectively. Passive coating 37 and active coating 38 have resistances $R_p$ and $R_a$ respectively. Analysis of circuitry 31 shows that as long as the sum of resistances $R1+R_a$ does not change with respect to the sum of resistances $R2+R_b$ then the signal to LED alarm 55 will remain constant. However, when the sum of resistances $R1+R_a$ changes with respect to the sum of resistances $R2+R_p$ then the signal to LED alarm 55 will vary. The LED or LCD alarm 55 will generate an alarm signal in response to a variance in the signal being inputted to LED or LCD alarm 55. Accordingly, the present system will detect either an increase or a decrease in the resistance due to adsorption on the active coating 38 and the LCD alarm 55 will go off in either situation. This is an important feature since, in some cases, vapor adsorption onto the active coating 38 may cause a reduction in the resistance of the active coating 38 whereas adsorption of other vapors may cause an increase in the resistance of the same active coating 38. In either case, it is important that the LCD alarm 55 be activated since any adsorption onto the surface of the active coating 38 is an indication of the oncoming exhaustion of the adsorbent bed. The dual sensor/bridge circuit approach of FIG. 3 is preferable to the sensor of FIG. 2 since fundamentally, measurement of null in a bridge circuit is a more sensitive method to measure changes in output signals, the temperature compensation is likely to be more exact with a pair of identical sensors, the circuitry for compensation is quite simple using a bridge circuit and the device will be less expensive, more uniform and more repeatable performance is obtained if the four electrodes on the chip are identical. Also, less processing of the chip is required. The additional measurement of impedances (complex and simple parts) can be accomplished between electrodes and are redundant. This redundancy is not required for operation nor utilized herein for simplicity. But in cases where it is advantageous to have several measurements of the same property (or several properties), the device illustrated herein can accommodate such applications.

An important consideration when employing an alarm device in accordance with the present invention is where in the filter 19 to locate the sensor portion 30. The location of the sensor portion 30 in the filter 19 will depend on several variables which include humidity, temperature, response time, the concentration profile of the adsorbent bed during exposure to vapor and the selected threshold level at which the alarm will be triggered to indicate oncoming exhaustion of the adsorbent bed. Each of these factors will have a bearing on the optimum location of the sensor portion 30 in the filter 19.

Generally, the location of the sensor portion 30 in the filter 19 is decided based on the sensitivity of the sensor portion 30 in combination with the margin of safety desired. The less sensitive the sensor portion 30 is, the closer to the inlet of the filter 19 it must be placed. In contrast, a very sensitive and reliable sensor may be placed near the outlet of the filter 19. The ideal sensor location can be affected by changing the selected threshold level of the alarm.

Another important factor in determining the location of the sensor portion 30 in the filter 19 is the breakthrough concentration curve of the adsorbent bed during vapor exposure. Generally, harmful vapors will enter the filter 19 through the screen opening 16 and spread out through the adsorbent material. As the vapors spread out they will be adsorbed and a concentration profile will be formed. Usually the highest concentrations will be detected at the point closest to the screen opening 16 and the concentration level will decrease as one moves away from the screen opening 16 in the filter 19. Since it is desirable to prevent any toxic vapors from reaching the pipe 17 the sensor portion 30 must be located such that the selected level concentration which sets off the alarm is reached at the location of sensor portion 30 prior to the time when toxic vapors reach the pipe 17. In this manner passage of toxic vapors into pipe 17 is prevented.

The concentration profile may be altered by humidity since humidity often reduces the efficiency of an adsorbent bed. Because of this reduced efficiency of the adsorbent bed there will be a gradual increase in the concentration of the vapor passing through the adsorbent bed rather than a sharp concentration front moving through the adsorbent bed as occurs when the adsorbent bed is functioning at peak efficiency. Thus, for use in high humidity, adjustments may be required.

The invention is further illustrated, but is not intended to be limited by, the following examples.

EXAMPLE 1

A microsensor in accordance with the present invention was fabricated by first depositing interdigitated gold electrodes on a silicon dioxide substrate and then spin coating the electrode arrays with a solution of silicone caulk, carbon and methylene chloride to deposit a thin film of vapor sensitive material on the electrodes. This carbon microsensor device operated as a chemiresistor.

Then the microsensor was connected to the alarm circuitry and placed in an adsorbent bed. The adsorbent bed was exposed to toxic gases and the resistance of the microsensor was monitored. At the point when the gases reached the microsensor a large change in its resistance was noted and the alarm went off indicating that the threshold level had been exceeded.

EXAMPLE 2

Figure 5A:
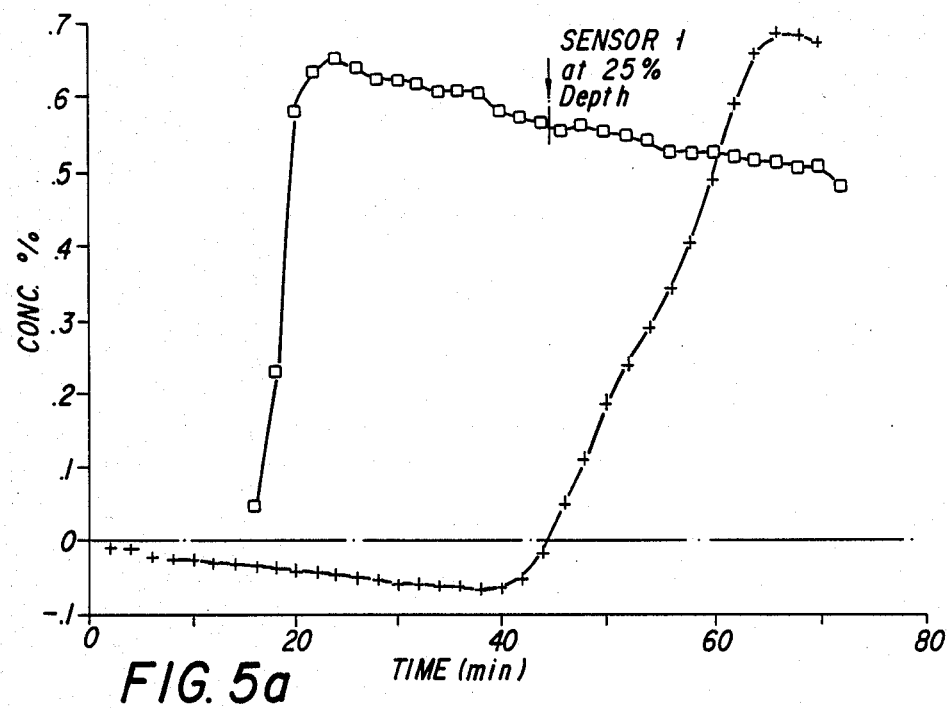
FIG. 5a is a graph of a breakthrough test for benzene with the sensor located at a depth of 25% from the inlet of the adsorbent bed.
Figure 5B:
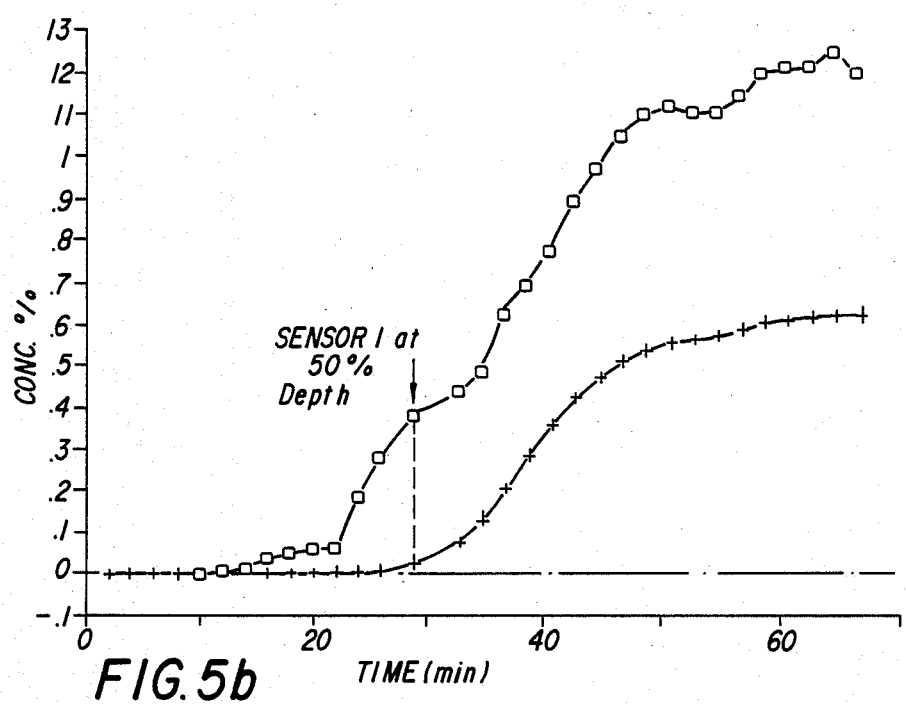
FIG. 5b is a graph of a breakthrough test for benzene with the sensor located at a depth of 50% from the inlet of the adsorbent bed.
Figure 5C:
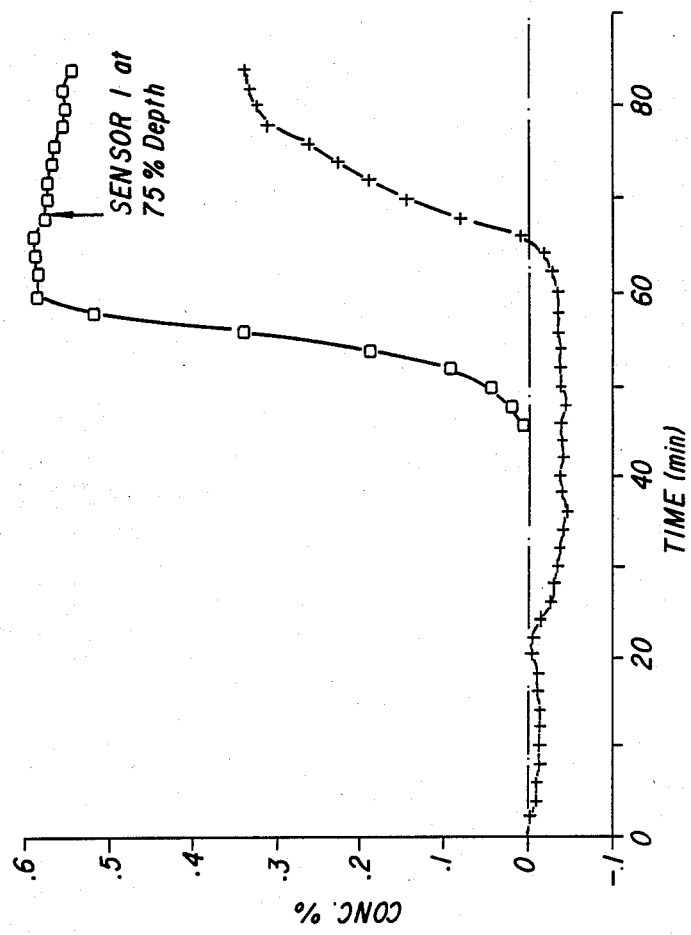
FIG. 5c is a graph of a breakthrough test for benzene with the sensor located at a depth of 75% from the inlet of the adsorbent bed.

Referring to FIGS. 5a, 5b and 5c, there are shown three different breakthrough curves for charcoal adsorbent beds exposed to benzene. The curves were determined by using two sensors. Sensor 1 is a sensor in accordance with the present invention and it monitors the concentration at different depths in the adsorbent bed, while sensor 2, a commercial SAW device, monitors the exit concentration of the adsorbent bed. Sensor 1 employed a vapor sensitive medium of a thin coating of charcoal and was fabricated by the method of Example 1. A concentration of 1% benzene vapor in dry air is fed to the adsorbent bed. The arrow on the graph indicates a concentration of 200 ppm (threshold level) at the bed exit.

From these graphs the threshold level for a given placement of the sensor in the adsorbent bed can be determined. For instance, for a sensor at 50% depth a threshold concentration setting of 0.4% will trigger the alarm at the point where the exit concentration is 200 ppm.

EXAMPLE 3

Figure 6A:
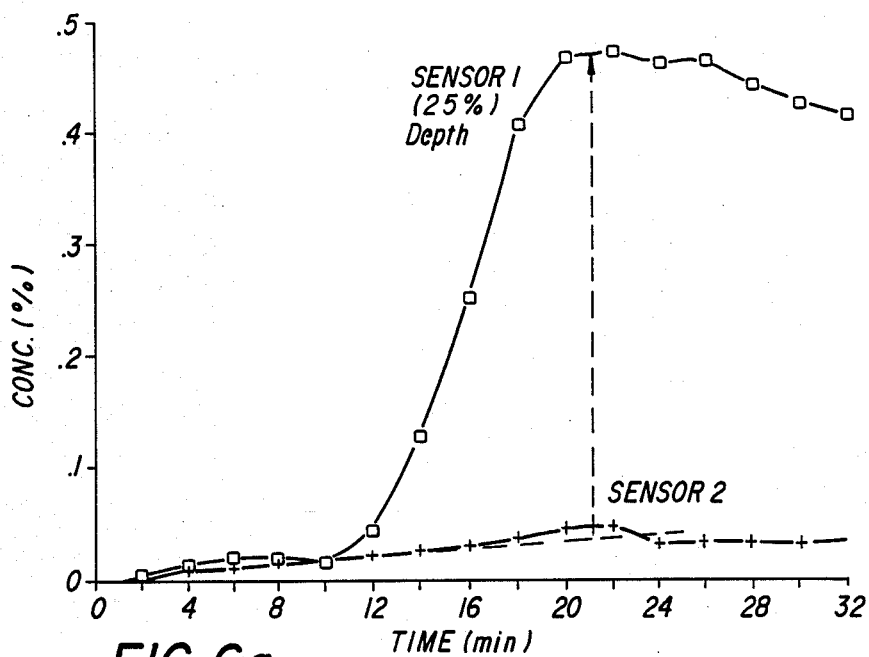
FIG. 6a is a graph of a breakthrough test for benzene with the sensor located at a depth of 25% from the inlet of a humidified adsorbent bed.
Figure 6B:
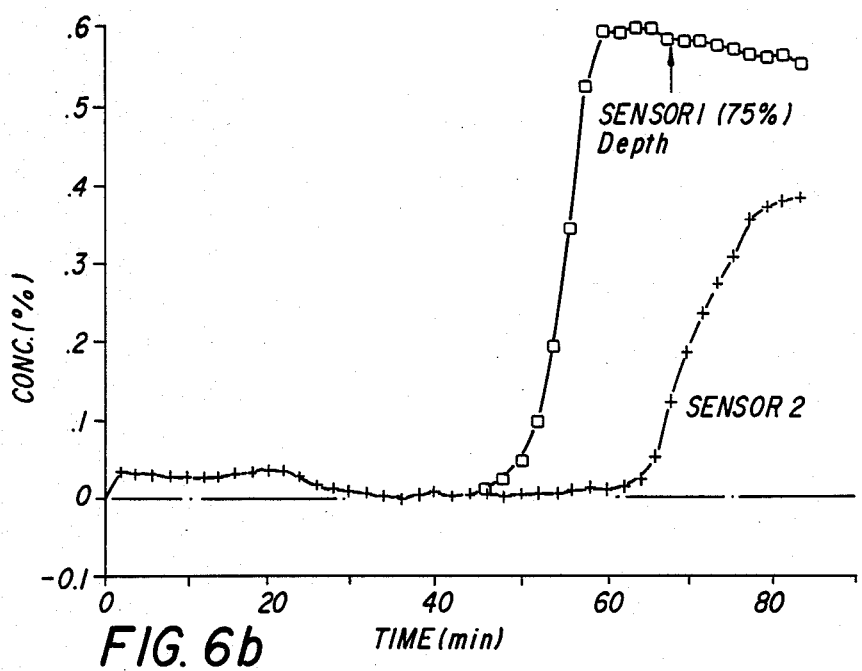
FIG. 6b is a graph of a breakthrough test for benzene with the sensor located at a depth of 75% from the inlet of a humidified adsorbent bed.

Referring to FIGS. 6a and 6b, there are shown two different breakthrough curves for charcoal adsorbent beds exposed to benzene. The curves were determined by using two sensors. Sensor 1 monitors the concentration at different depths in the adsorbent bed, while sensor 2 monitors the exit concentration of the adsorbent bed. Sensor 1 is a sensor in accordance with the present invention employing a vapor sensitive medium of charcoal and was fabricated by the method of Example 1. Sensor 2 is a commercially available SAW device. A concentration of 1% benzene vapor in humidified air is fed to the adsorbent bed to show the effects of humidity on the breakthrough curve. The arrow on the graph indicates a concentration of 200 ppm (threshold level) at the bed exit.

From these graphs the threshold level for a given placement of the sensor in the adsorbent bed can be determined. It should be noted that the sensor responds more gradually in humidified air and a lower overall response is generated.

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. Accordingly, the scope of the invention is to be determined by the claims appended hereto.

What is claimed is:

1. A sensor useful in detecting the exhaustion of an adsorbent bed comprising:
   a vapor sensitive medium having a response to the vapors adsorbed by the adsorbent bed which is substantially the same as the response of the adsorbent bed to the vapors adsorbed, and
   means for monitoring a property of said vapor sensitive medium that is a function of the response of said vapor sensitive medium to the vapors adsorbed by the adsorbent bed.

2. A sensor as claimed in claim 1 wherein said vapor sensitive medium comprises at least some of the same material used as the adsorbent bed.

3. A sensor as claimed in claim 2 further comprising a means for providing temperature compensation of the sensor.

4. A sensor as claimed in claim 3 further comprising a means for providing humidity compensation of the sensor.

5. A sensor as claimed in claim 3 wherein said means for monitoring comprises electrodes or electrical contacts.

6. A sensor as claimed in claim 5 wherein said means for providing temperature compensation comprises at least one reference electrode.

7. A sensor as claimed in claim 2 wherein said vapor sensitive medium is up to 0.1 cm in thickness.

8. A sensor as claimed in claim 1 wherein the adsorbent bed and said vapor sensitive medium comprise carbon.

9. An adsorbent bed safety alarm system for detecting and signalling the exhaustion of an adsorbent bed, said alarm system comprising:

a sensor means including a vapor sensitive medium having a response to the vapors adsorbed by the adsorbent bed which is substantially the same as the response of the adsorbent bed to the vapors being adsorbed, and means for monitoring a property of said vapor sensitive medium that is a function of the response of said vapor sensitive medium to the vapors adsorbed by the adsorbent bed, and a means for generating an alarm signal responsive to a change in the property of said vapor sensitive medium monitored by said means for monitoring.

10. An adsorbent bed safety alarm system as claimed in claim 9 wherein said vapor sensitive medium comprises at least some of the same material used as the adsorbent bed.

11. An adsorbent bed safety alarm system as claimed in claim 10 wherein said sensor further comprises a means for providing temperature compensation of said sensor means.

12. An adsorbent bed safety alarm system as claimed in claim 11 further comprising a means for providing humidity compensation of said sensor.

13. An adsorbent bed safety alarm system as claimed in claim 9 wherein the adsorbent bed and said vapor sensitive medium comprise a material selected from the group consisting of carbon, silica, silica gel, alumina, molecular sieves and drying agents.

14. An adsorbent bed safety alarm system as claimed in claim 9 wherein said means for generating an alarm signal comprises:

a means for preventing alarm signal generation until the change in the monitored property exceeds a threshold amount.

15. An adsorbent bed safety alarm system as claimed in claim 14 further comprising:

a means for selecting the threshold level for said means for determining.

16. An apparatus for use in adsorbing harmful or undesirable vapors that signals the exhaustion of the adsorbent material to prevent flow of harmful or undesirable vapors through the apparatus, said apparatus comprising:

a housing having an inlet means and an outlet means, an adsorbent bed housed within said housing, a sensor means located in said adsorbent bed, said sensor means including a vapor sensitive medium having a response to the vapors adsorbed by the adsorbent bed which is substantially the same as the response of the adsorbent bed to the vapors being adsorbed, and means for monitoring a property of said vapor sensitive medium that is a function of the response of said vapor sensitive medium to the vapors adsorbed by the adsorbent bed, and a means for generating an alarm signal responsive to a change in the property of said vapor sensitive medium monitored by said monitoring means.

17. An apparatus as claimed in claim 16 wherein said vapor sensitive medium comprises at least some of the same material used as the adsorbent bed.

18. An apparatus as claimed in claim 17 wherein said adsorbent bed and said vapor sensitive medium comprise carbon.

19. An apparatus as claimed in claim 17 wherein said sensor means further comprises a means for providing temperature compensation of said sensor means.

20. An apparatus as claimed in claim 16 wherein said means for generating an alarm signal further comprises:

a means for preventing alarm signal generation until the change in the monitored property exceeds a threshold amount.

* * * * *